United States Patent [19]

Itoh et al.

[11] Patent Number: 5,487,900

[45] Date of Patent: Jan. 30, 1996

[54] STABILIZED VITAMIN D PREPARATION

[75] Inventors: Hiroki Itoh, Takarazuka; Tetsuro Tabata; Jun-Ichi Kikuta, both of Osaka, all of Japan

[73] Assignee: Takeda Chemical Industries, Limited, Osaka, Japan

[21] Appl. No.: 193,650

[22] Filed: Feb. 7, 1994

Related U.S. Application Data

[63] Continuation of Ser. No. 865,613, Apr. 9, 1992, abandoned.

[30] Foreign Application Priority Data

| Apr. 9, 1991 | [JP] | Japan | 3-076210 |
| Feb. 4, 1992 | [JP] | Japan | 4-019099 |

[51] Int. Cl.$^6$ ........................ A61K 9/48
[52] U.S. Cl. ............. 424/451; 424/465; 424/468; 424/489
[58] Field of Search .................... 424/451, 465, 424/468

[56] References Cited

U.S. PATENT DOCUMENTS

| 4,729,895 | 3/1988 | Makino et al. | 424/465 |
| 4,801,460 | 1/1989 | Goertz | 424/468 |

FOREIGN PATENT DOCUMENTS

| 0191489 | 8/1986 | European Pat. Off. . |
| 0413828 | 2/1991 | European Pat. Off. . |

*Primary Examiner*—Thurman K. Page
*Assistant Examiner*—William E. Benston, Jr.
*Attorney, Agent, or Firm*—Foley & Lardner

[57] ABSTRACT

Heat-labile vitamin D is dispersed in a basic polymer and an excipient readily soluble in an organic solvent to provide a pharmaceutical composition. The composition exhibits reduced isomerization, decomposition, and discoloration while showing excellent stability.

17 Claims, No Drawings

STABILIZED VITAMIN D PREPARATION

This application is a continuation of U.S. application Ser. No. 07/865,613, filed Apr. 9, 1992, abandoned.

FIELD OF THE INVENTION

This invention relates to a stabilized preparation of a heat-labile vitamin D active compound (hereinafter it may be referred to briefly as "active vitamin D") and a method of preparing same.

BACKGROUND OF THE INVENTION

Since active vitamin D is chemically unstable to heat, light, oxygen and moisture, it is very important to provide it in the form of a stabilized preparation.

Conventionally, as methods for stabilizing such active vitamin D in the solid state, have been proposed the inclusion of a heat-labile vitamin $D_3$ active compound (hereinafter it may be referred to briefly as "active vitamin $D_3$") with cyclodextrin [Published unexamined patent application 128417/1976], the complex formation with cholesterols [Published examined patent application 51948/1987], the formation of the outer layer containing an active vitamin $D_3$ and an excipient which is soluble in an organic solvent, for example, polyvinylpyrrolidone or hydroxypropyl cellulose on the inner layer comprising an excipient which is insoluble in an organic solvent, for example, lactose or crystalline cellulose [U.S. Pat. No. 4,729,895] or the like.

However, preparations provided by conventional methods of stabilization are directed to active vitamin $D_3$, and, besides, these preparations are not stable enough under conditions of high temperature and humidity, which is counted, among other factors, as a drawback.

Furthermore, these methods for stabilization of active vitamin $D_3$ are not applicable to stabilization of a heat-labile vitamin $D_2$ active compound (hereinafter it may be referred to briefly as "active vitamin $D_2$") as they are.

Under such circumstances as above, the present inventors examined the influence of pH on the stability of active vitamin $D_2$. More specifically, to a Britton-Robinson broad range buffer solution (90 ml) was added an ethanol solution of 1α-hydroxy vitamin $D_2$ (1α—OH—$D_2$) (1 ml, containing 32 μg of 1α—OH—$D_2$), and the mixture was stored at 25 C. After six hours and 22 hours, the respective residual rates of 1α—OH—$D_2$ were examined. The results are shown in Table 1.

TABLE 1

| Conditions | Period | pH3 | pH5 | pH7 | pH9 | pH10 |
|---|---|---|---|---|---|---|
| Residual content (%) of 1α-OH-$D_2$ | 6 hr | 48.0 | 52.2 | 67.5 | 87.0 | 88.6 |
| | 22 hr | 20.2 | 30.4 | 54.2 | 85.9 | 88.3 |

Method of Determining Residual Content
Apparatus: Shimadzu LC-6AD
Column: YMC-PACK A-202 S-5 120A C8
Volume of Sample: 150 μl (Conc. of Sample 147.2 ng/ml)
Column Pressure: 25 kg/cm$^2$
Column Temperature: 40° C.
Mobile Phase: acetonitrile:water = 75:25 (V/V)
Flow Rate: 1 ml/min
Detector: UV detector 265 nm As is clear from Table 1, it was revealed that 1α—OH—$D_2$ was stabilized at pH 9 and higher. Based on this finding, the present inventors have further made intensive research and accomplished the present invention.

SUMMARY OF THE INVENTION

Thus, the present invention relates to
1. a composition of a heat-labile vitamin D active compound, which comprises a heat-labile vitamin D active compound being dispersed in a basic polymer,
2. a composition of a heat-labile vitamin $D_2$ active compound, which comprises an excipient which is soluble in an organic solvent, a heat-labile vitamin $D_2$ active compound and a basic substance,
3. a composition, which comprises a finely pulverized heat-labile vitamin D active compound being dispersed homogeneously in a basic substance and an excipient which is soluble in water.

DETAILED DESCRIPTION OF THE PREFERRED EMBODIMENT

Examples of the active vitamin D and the active vitamin D in the finely pulverized vitamin D to be employed in the present invention include active vitamin $D_2$ and active vitamin $D_3$, preferably active vitamin $D_2$.

Examples of the active vitamin $D_2$ compound include 1α-hydroxy vitamin $D_2$ (1α—OH—$D_2$), 1α,24,25-trihydroxy vitamin $D_2$ (1α,24,25-(OH)$_3$-$D_2$), 1α-hydroxy-24-oxo vitamin $D_2$, 24-hydroxy vitamin $D_2$ (24—OH—$D_2$), 24,25-dihydroxy vitamin $D_2$ (24,25—(OH)$_2$—$D_2$), 25-hydroxy vitamin $D_2$ (25—OH—$D_2$) and 1α, 25-dihydroxy vitamin $D_2$ (1α,25—(OH)$_2$—$D_2$).

Among these active vitamin $D_2$ compound, 1α-hydroxy vitamin $D_2$ is preferred.

Examples of the active vitamin $D_3$ compound include an active vitamin $D_3$ bearing a hydroxyl group in the 1α-position, such as 1α-hydroxy vitamin $D_3$(1α—OH—$D_3$), 1α,25-dihydroxy vitamin $D_3$ (1α,25—(OH)$_2$—$D_3$), 1α,24-dihydroxy vitamin $D_3$(1α,24—(OH)$_2$—$D_3$), 1α,24,25-trihydroxy vitamin $D_3$(1α,24,25—(OH)$_3$—$D_3$), 1α-hydroxy-24-oxo vitamin $D_3$, 1α,25-dihydroxy-24-oxo vitamin $D_3$, 1α,25-dihydroxy vitamin $D_3$-26,23-lactone, 1α,25-dihydroxy vitamin $D_3$-26,23-peroxy lactone, and 26,26,26,27,27-hexafluoro-1α,25-dihydroxy vitamin $D_3$: or an active vitamin $D_3$ compound bearing no hydroxyl group in the 1α-position, such as 25-hydroxy vitamin $D_3$(25—OH—$D_3$), 24-hydroxy vitamin $D_3$(24—OH—$D_2$), 24-oxo vitamin $D_3$, 24,25-dihydroxy vitamin $D_2$ (24,24—(OH)$_2$—$D_3$), 25-hydroxy-24-oxo vitamin $D_3$, 25-hydroxy vitamin $D_3$ -26,23-lactone, and 25-hydroxy vitamin $D_2$-26,23-peroxylactone.

Among these active vitamin $D_3$ compounds, 1α—OH—$D_3$, 1α, 25—(OH)$_2$—$D_3$, 1α,24—(OH)$_2$—$D_2$, and 1α,25-dihydroxy vitamin $D_3$-26,23-lactone are preferred.

The basic polymer to be employed in the present invention is exemplified by a basic synthetic polymer having the molecular weight ranging from about 5,000 to 300,000, preferably about 10,000 to 200,000. The pH's of the aqueous solution (2.0 w/v %) of said basic synthetic polymers are 7.5 or more, preferably about 8.0 to 13.0.

Preferable examples of the above-mentioned basic synthetic polymer include, among others, vinyl acetate polymer derivatives [e.g. polyvinyl acetal diethyl aminoacetate (AEA)] and (meth)acrylic acid copolymer derivatives (e.g. aminoalkyl methacrylate copolymer E). Among these, vinyl acetate polymer derivatives [e.g. polyvinyl acetal diethyl aminoacetate (AEA)] is especially preferable.

Examples of the excipient to be employed in the present invention, which is soluble in an organic solvent, include a synthetic polymer which is soluble in an organic solvent

[e.g. polyvinyl pyrrolidone (PVP)], a semi-synthetic polymer which is soluble in an organic solvent [e.g. cellulose derivatives such as hydroxypropylcellulose (HPC), hydroxypropylmethylcellulose (HPMC) and methyl cellulose (MC)] and a sterol derivative which is soluble in an organic solvent [e.g. cholesterol, β-sitosterol, campesterol and deoxycholic acid]. Among them, the synthetic polymer which is soluble in an organic solvent [e.g. polyvinyl pyrrolidone (PVP)] and the semi-synthetic polymer which is soluble in an organic solvent [e.g. cellulose derivatives such as hydroxypropylcellulose (HPC), hydroxypropylmethylcellulose (HPMC) and methyl cellulose (MC)] are preferable. Especially preferable are polyvinyl pyrrolidone, hydroxypropylcellulose and hydroxypropylmethylcellulose.

The basic substances to be employed in the present invention are exemplified by alkali metal salts of 2-6 C organic carboxylic acid (e.g. sodium acetate, potassium acetate and sodium citrate), alkaline earth metal oxides (e.g. calcium oxide and magnesium oxide), alkali metal carbonates or hydrogencarbonates (e.g. potassium carbonate, sodium carbonate and sodium hydrogencarbonate), alkaline earth metal carbonates (e.g. magnesium carbonate and calcium carbonate), alkali metal phosphates (e.g. disodium hydrogenphosphate, dipotassium hydrogenphosphate and trisodium phosphate) and an alkali metal pyrophosphate (e.g. potassium pyrophosphate and sodium pyrophosphate). Among these basic substances, sodium salts of a 2-6 C organic carboxylic acid (e.g. sodium acetate and sodium citrate), oxides of magnesium (e.g. magnesium oxide), alkali metal carbonates or hydrogencarbonates (e.g. potassium carbonate, sodium carbonate and sodium hydrogencarbonate), magnesium carbonate, alkali metal phosphates (e.g. disodium hydrogencarbonate, dipotassium hydrogen carbonate and trisodium phosphate) and alkali metal pyrophosphates (e.g. potassium pyrophosphate and sodium pyrophosphate) are preferred. Especially preferable are sodium citrate, magnesium oxide, alkali metal carbonates or hydrogencarbonates (e.g. potassium, sodium carbonate and sodium hydrogencarbonate), alkali metal phosphates (e.g. disodium hydrogenphosphate, dipotassium hydrogenphosphate and trisodium phosphate).and alkali metal pyrophosphates (e.g. potassium pyrophosphate and sodium pyrophosphate).

The excipient which is soluble in water to be employed in the present invention is exemplified by a polymer which is soluble in water.

Preferable examples of the polymer which is soluble in water include a natural polymer which is soluble in water, a synthetic polymer which is soluble in water and a semi-synthetic polymer which is soluble in water. Among them, a semi-synthetic polymer which is soluble in water is especially preferable.

Desirable practical examples of the above-mentioned natural polymer which is soluble in water include starch derivatives (e.g. dextran and pullulan), protein (e.g. gelatin and albumin) and marine algae (e.g. agar and sodium alginate). Among them, starch derivatives (e.g. dextran and pullulan) are especially desirable.

Desirable practical examples of the above-mentioned synthetic polymer which is soluble in water include polyvinyl pyrrolidone, polyvinyl alcohol, polyethylene glycol, polyacrylic acid and polymethacrylic acid. Among them, polyvinyl pyrrolidone is especially desirable.

Desirable practical examples of the above-mentioned semi-synthetic polymer which is soluble in water include cellulose derivatives (e.g. hydroxypropylcellulose, methyl cellulose, hydroxypropylmethylcellulose and sodium carboxymethyl cellulose). Among these, hydroxypropylcellulose is especially desirable.

These excipients which are soluble in water may be used singly or as a mixture of two or more species of them in a suitable ratio.

The composition of a heat-labile vitamin D active compound, which comprises a heat-labile vitamin D active compound being dispersed in a basic polymer is prepared by, for example, the following method. A solution of an active vitamin D in an alcohol solvent (e.g. methanol, ethanol and propanol, preferably ethanol) is added to a solution of a basic polymer in an alcohol solvent (e.g. methanol, ethanol and propanol, preferably ethanol), and the mixture is blended by stirring sufficiently; then to the resultant solution is added a diluent (e.g. lactose, mannitol, cyclodextrin, casein and starch), and the mixture is sufficiently blended to give a homogeneous solution, followed by distilling off the alcohol solvent.

In the above method, the amount of the basic polymer is usually in the range of from about 100 to 5000 weight parts, preferably from about 200 to 4000 weight parts, especially preferably from about 300 to 3000 weight parts, relative to one weight part of the active vitamin D. The amount of the alcohol solvent to be used ranges usually from about 1 to 100 weight parts, preferably from about 1 to 50 weight parts, relative to one weight part of the basic polymer. The diluent may be used singly or as a mixture of two or more species in a suitable ratio. The amount of the diluent to be used ranges usually from about 1 to 300 weight parts, preferably from about 5 to 200 weight parts, especially preferably from about 10 to 100 weight parts.

The composition of a heat-labile vitamin $D_2$ active compound, which comprises an excipient which is soluble in an organic solvent, a heat-labile vitamin $D_2$ active compound and a basic substance, can be prepared by, for example, the following method. An active vitamin $D_2$ and an excipient which is soluble in an organic solvent are blended by sufficiently stirring in an organic solvent capable of dissolving both the active vitamin $D_2$ and the excipient which is soluble in an organic solvent; then to the resultant solution are added a basic substance and, when desired, a diluent (e.g. lactose, mannitol, cyclodextrin, casein and starch), and the mixture is blended sufficiently to give a homogeneous solution, followed by distilling off the organic solvent.

In the above method, the amount of the excipient readily soluble in an organic solvent ranges usually from about 100 to 5000 weight parts, preferably from about 300 to 4000 weight parts, especially preferably from about 500 to 2500 weight parts, relative to one weight part of the active vitamin $D_2$. The .amount of the basic substance to be employed corresponds, for example, to that required for keeping the pH of the moisture penetrating in the solid preparation containing the composition according to the present invention in the alkaline region under high temperature and humidity. Since the amount depends upon the amount of the excipient readily soluble in an organic solvent, and the amounts and properties of known additives (e.g. diluents, binders, disintegrants and lubricants) to be employed for preparing a solid composition with a vitamin $D_2$ composition prepared according to the present invention, it cannot be stated simply, but it usually ranges from about 10 to 100000 weight parts, preferably about 100 to 70000 weight parts, especially preferably about 200 to 50000 weight parts, relative to one weight part of the active vitamin $D_2$. In the case of using a diluent when desired, it may be used singly or as mixture of two or more species in a suitable ratio, and the amount ranges usually from about 1 to 300 weight parts, preferably from about 5 to 200 weight parts, especially preferably from about 10 to 150 weight parts relative to one weight part of the excipient which is soluble in an organic solvent.

Examples of the organic solvent to be employed include an alcohol such as methanol, ethanol and propanol; a halogenated hydrocarbon such as dichloromethane and chloroform; and an ether such as diethyl ether. Among them, an alcohol such as methanol and ethanol is especially preferable. Organic solvents may be used by mixing two or more species. In such an organic solvent as above, active vitamin $D_2$ and a excipient readily soluble in an organic solvent are dissolved. The amount of the organic solvent ranges usually from about 1 to 1000 weight parts, preferably from about 1 to 100 weight parts relative to one weight part of the excipient which is soluble in an organic solvent.

The composition, which comprises a finely pulverized heat-labile vitamin D active compound being dispersed homogeneously in a basic substance and an excipient which is soluble in water, can be prepared by, for example, the following method. Active vitamin D and an excipient which is soluble in water are suspended in a solvent (e.g. water) which does not dissolve the active vitamin D and dissolves the excipient which is soluble in water, then the active vitamin D is pulverized by means of a wet grinding machine [e.g. Microfluidizer (Microfluidics Inc., USA)]. The average diameter of the pulverized active vitamin D is preferably 5 μm or less. To thus-processed dispersion are added a basic substance and an excipient which is soluble in water, and further, when desired, a diluent and/or an oily substance having a low melting point, which is blended sufficiently to give a homogeneous mixture, followed by granulation in accordance with a per se conventional method.

In the above-mentioned method, the total amount of the excipient which is soluble in water ranges usually from about 100 to 5000 weight parts, preferably from about 300 to 4000 weight parts, especially preferably from about 500 to 2000 weight parts, relative to one weight part of the active vitamin D.

The amount of the basic substance ranges, though it depends on kinds of the basic substance employed, from about 100 to 2000 weight parts, preferably from about 200 to 1500 weight parts, especially preferably from about 300 to 1000 weight parts, relative to one weight part of the finely pulverized active vitamin D.

In the above-mentioned method, the diluent to be used when desired is any one which is employed in conventional formulation processes, which is exemplified by lactose, mannitol, cyclodextrin, casein and starch (e.g. corn starch).

These diluents may be used singly or as a mixture of two or more species in a suitable ratio.

The amount of these diluents ranges usually from about 1 to 300 weight parts, preferably from about 5 to 200 weight parts, especially preferably from about 10 to 150 weight parts, relative to one weight part of the excipient which is soluble in water.

In the above-mentioned method, the oily substance having low melting point to be used when desired can be any one which has a low melting point (e.g. about 20° to 90° C.) and does not have a bad influence on the active vitamin D.

Example of the oily substance having a low melting point include a homopolymer or copolymer of alkylene oxide.

Among these oily substances having a low melting point, a homopolymer of alkylene oxide is preferred.

Example of the alkylene oxide include, for example, ethylene oxide, propylene oxide, trimethylene oxide and tetrahydrofurane. Especially preferable is ethylene oxide.

The homopolymer of alkylene oxide to be employed in the present invention has preferably a molecular weight of about 1,000 to 10,000 (e.g. polyethylene glycol 6000).

The copolymer of alkylene oxide to be employed in the present invention has preferably a molecular weight of about 1,000 to 10,000 (e.g. copolymer of ethylene oxide and propylene oxide, copolymer of ethylene oxide and trimethylene oxide).

These oily substances having a low melting point may be used singly or as a mixture of two or more species in a suitable ratio.

The amount of these oily substances having a low melting point ranges usually from about 0.1 to 15 weight parts, preferably from about 0.3 to 13 weight parts, especially preferably from about 0.4 to 10 weight parts, relative to one weight part of the excipient which is soluble in water.

In the pharmaceutical composition prepared by the above-mentioned method, the active form of finely pulverized vitamin D and the basic substance are brought into contact with each other homogeneously or closely.

The pharmaceutical composition of this invention may be, when needed, additionally incorporated with other suitable excipients (e.g. diluents, binders, disintegrants, antioxidants, antioxidant enhancers, colorants, lubricants and oily substances having low melting point). The pharmaceutical composition of this invention can be prepared into orally administrable preparations, for example, solid preparations such as tablets, capsules (e.g. hard capsules or soft capsules), granules and powders, and liquid preparations such as syrup, emulsion and suspension. Among them, solid preparations such as tablets, capsules (e.g. hard capsules or soft capsules), granules and powders are especially preferable.

The diluents to be employed for the orally administrable preparations are, for example, starch (e.g. corn starch), crystalline cellulose, dextrin, lactose, mannitol, sorbitol, anhydrous calcium phosphate, sucrose, talc (naturally occurring magnesium silicate hydrate), kaolin, precipitated calcium carbonate, sodium chloride, titanium oxide and lightweight anhydrous silicic acid; the binders are, for example, starch, dextrin, tragacanth gum, gelatin, polyvinyl pyrrolidone, polyvinyl alcohol, hydroxypropylcellulose, crystalline cellulose, hydroxypropylmethylcellulose, ethyl cellulose, carboxymethylcellulose and arabic gum; the disintegrants are, for example, starch, crystalline cellulose, carboxymethylcellulose calcium and agar-agar powder; the antioxidants are, for example, butyl hydroxytoluene (BHT), propyl gallate, butyl hydroxyanisole (BHA), lecithin, α-tocopherol, hydroquinone, octyl gallate, dodecyl gallate, isoamyl gallate, nordihydroguaialetic acid, guaiac resin, α-naphthylamine, ethyl protocathecuate (EPG), ascorbic acid stearate ester, ascorbic palmitate ester, cysteine hydrochloride, sodium ascorbic stearate, thioglycerol and thiosorbitol; the antioxidant enhancers are, for example, dihydroethylglycine, ethylenediaminetetraacetic acid, glycerol, phenylalanine, sorbitol and tryptophan; the colorants are, for example, tar pigments whose use in medicines is approved by the Welfare Ministry; and the lubricants are, for example, talc, starch, magnesium and calcium stearate, boric acid, paraffin, cocoa butter, macrogol, leucine and sodium benzoate; and the oily substances having a low melting point are the same as aforementioned.

The orally administrable preparations may be coated by a coating agent for the purpose of shading, masking of the taste or sustained release property.

Usable as coating agents are, for example, hydroxypropylmethylcellulose, ethylcellulose, hydroxymethylcellulose, hydroxypropylcellulose, polyoxyethylene glycol, Tween 80, Pluorinc F68, and pigments such as titanium oxide and ferric oxide.

An ordinary coating agent which is used in conventional solid preparation formulation processes and does not have a bad influence on the active vitamin D in the orally administrable preparations can be used for the coating agent to be employed in the present invention.

Among the coating agents, a coating agent for shading is preferred.

Examples of the coating agent for shading include ferric oxide and titanium oxide.

The orally administrable preparation is coated in accordance with a pre se conventional method.

In the composition of this invention, thermal isomerization, decomposition or discoloration is remarkablly reduced, keeping excellent stability.

The pharmaceutical preparation of active vitamin D according to the present invention is of low toxicity and effective for, among others, prophylaxis or therapy of osteoporosis in man. In the case of administering the active vitamin D of this invention to an adult (body weight 50 kg) orally or non-orally, the daily dose ranges, though it is variable with kinds of vitamin D contained, from about 0.1 to 10 μg, preferably from about 0.5 to 8 μg, especially preferably from about 1 to 5 μg, in 1–3 installments.

EXAMPLE 1

In 2 ml of ethanol was dissolved 0.8 mg of 1α—OH—D$_2$, which was added to 10 ml of an ethanol solution dissolving 1 g of polyvinylacetal diethylaminoacetate (AEA), then the mixture was stirred for 10 minutes. This solution was mixed with 39 g of lactose, and the mixture was kneaded. The resultant mixture was dried in vacuo at 25° C. for 16 hours, then the ethanol was distilled off. This dry product was crushed in a mortar and sieved through 32 mesh screen to provide the 1α—OH—D$_2$ composition. This composition was kept at a thermo-hydrostat which was controlled to 40° C. and 75% relative humidity so that the residual percentage of 1α—OH—D$_2$ was examined with the lapse of time. As the control, a composition prepared in the same manner using hydroxypropylcellulose instead of AEA was employed. As shown clearly in Table 2, the composition of this invention is more stable than the control composition under high temperature and humidity.

TABLE 2

| Conditions | Period | This invention | Control |
|---|---|---|---|
| Residual content (%) of 1α-OH-D$_2$ at 40° C. 75% RH | 2 weeks<br>4 weeks | 103.3<br>101.8 | 87.9<br>78.6 |

Method of determining the residual content
Apparatus: Shimadzu LC-6AD
Column: YMC-PACK A-202 S-5 120A C8
Amount of Sample: 150 1 (Conc. of Sample 147.2 ng/ml)
Column pressure: 25 kg/cm²
Column temperature: 40° C.
Mobile phase: acetonitrile:water = 75:25 (V/V)

EXAMPLE 2

In 2 ml of ethanol was dissolved 0.8 mg of 1α—OH—D$_2$, which was added to 10 ml of an ethanol solution dissolving 1 g of hydroxypropylcellulose, then the mixture was stirred for 10 minutes. This solution was mixed with 19.5 g of disodium hydrogen phosphate and 19.5 g of lactose, and the mixture was kneaded. The resultant mixture was dried in vacuo at 25° C. for 16 hours, then the ethanol was distilled off. This dry product was crushed in a mortar and sieved through 32 mesh screen to provide the 1α—OH—D$_2$ composition. This composition was kept in a thermo-hydrostat which was controlled to 40° C. and 75% relative humidity so that the residual percentage of 1α—OH—D$_2$ was examined with the lapse of time. As the control, the same one as used in Example 1 was employed. As shown clearly in Table 3, the composition of this invention is more stable than the control composition under high temperature and humidity.

TABLE 3

| Conditions | Period | This invention | Control |
|---|---|---|---|
| Residual content (%) of 1α-OH-D$_2$ at 40° C. 75% RH | 2 weeks<br>4 weeks | 105.1<br>96.5 | 87.9<br>78.6 |

Method of determining the residual content
Device: Shimadzu LC-6AD
Column: YMC-PACK A-202 S-5 120A C8
Amount of Sample: 150 μl (Conc. of Sample 147.2 ng/ml)
Column pressure: 25 kg/cm²
Column temperature: 40° C.
Mobile phase: acetonitrile:water = 75:25 (V/V)
Flow rate: 1 ml/min
Dectector: UV detector 265 nm

EXAMPLE 3

A mixture of 75 weight parts of the 1α—OH—D$_2$ composition of Example 1, 24.5 weight parts of corn starch and 0.5 weight part of magnesium stearate was subjected to tabletting by means of a rotary tabletting machine to provide tablets of 6.5 mm diameter and about 2.5 mm thickness. The weight of each tablet was about 100 mg, and each tablet contained about 1.5 μg of 1α—OH—D$_2$.

EXAMPLE 4

To 180 ml of an aqueous solution dissolving 3.6 g of hydroxypropylcellulose was added 6 mg of 1α—OH—D$_2$, which was subjected to crushing by means of a wet grinder machine, Microfluidizer (Microfluidics Inc., USA). In this dispersion were dissolved 5.4 g of hydroxypropylcellulose and 4.5 g of disodium hydrogenphosphate. Using this dispersion as the binder, 213 g of D-mannitol and 61.5 g of corn starch were subjected to granulation by means of a fluidized-bed granulator FD-3S (Powrex Inc., Japan). The granules were sieved through 32 mesh screen to provide the 1α—OH—D$_2$ composition. This composition contained no thermal isomer. This composition of the present invention was stored in a thermo-hydrostat at 40° C. and 75% relative humidity so that the residual percentage of 1α—OH—D$_2$ was examined with the lapse of time. As the control, the same one as used in Example 1 was employed. As shown clearly in Table 4, the composition of this invention is more stable than the control composition under high temperature and humidity, with less formation of thermal isomers.

TABLE 4

| Conditions | Period | This invention (Example 4) | Control |
| --- | --- | --- | --- |
| Residual | 0 weeks | 100.0 (0.0) | 93.3 (6.7) |
| content (%) | 2 weeks | 95.9 (2.1) | 76.6 (9.0) |
| of 1α-OH-D$_2$ | 4 weeks | 92.6 (2.3) | 63.0 (8.1) |

Values in parentheses show content of thermal isomer.
Method of determining the residual content
Apparatus: Shimadzu LC-6AD
Column: YMC-PaCK A-202 S-5 120A C8
Amount of Sample: 150 1 (Conc. of Sample 1.0 μg/ml)
Column pressure: 25 kg/cm$^2$
Column temperature: 40° C.
Mobile phase: acetonitrile:water = 75:25 (V/V)
Flow rate: 1 ml/min
Detector: UV detector 265 nm

EXAMPLE 5

A mixture of 240.0 g of the 1α—OH—D$_2$ composition prepared in Example 4, 8.3 g of corn starch and 1.7 g of magnesium stearate was subjected to tabletting by means of a rotary tabletting machine to provide tablets. Each tablet is of a size of 6.5 mm in diameter and about 2.5 mm in thickness, and has a weight of 100.0 mg. By the Mini-Hi-Coater (Freund A. G., Japan), 200.0 g of these tablets were coated with 10.0 g of a film component consisting of 74.8 weight parts of hydroxypropylmethylcellulose, 15 weight parts of polyethylene glycol, 10 weight parts of titanium oxide and 0.2 weight parts of ferric oxide. Each of these tablets contained about 2.0 μg of 1α—OH—D$_2$.

EXAMPLE 6

To 180 ml of an aqueous solution of 3.6 g of hydroxypropylcellulose was added 6 mg of 1α—OH—D$_2$, which was subjected to crushing by means of a wet grinding machine, Microfluidizer (Microfluidics Inc., USA). In this dispersion were dissolved 5.4 g of hydroxypropylcellulose, 4.5 g of disodium hydrogenphosphate and 6.0 g of polyethylene glycol. Using this dispersion as binder, 207.0 g of D-mannitol and 61.5 g of corn starch were subjected to granulation by means of a fluidized-bed granulator FD-3S (Powrex Inc., Japan). The granules were sieved through a 32 mesh screen to provide a 1α—OH—D$_2$ composition. A mixture of 240.0 g of this 1α—OH—D$_2$ composition, 8.3 g of corn starch and 1.7 g of magnesium stearate was subjected to tabletting by means of a rotary tabletting machine to provide tablets. Each of these tablets is of a size of 6.5 mm in diameter and about 2.5 mm in thickness, and has a weight of 100.0 mg. Each of these tablets contained about 2.0 μg of 1α—OH—OH—D$_2$.

What we claim is:

1. A composition of a heat-labile active vitamin D$_2$ compound, which comprises an aqueous solution of a heat-labile active vitamin D$_2$ compound being dispersed in a basic polymer selected from the group consisting of vinyl acetate polymers and acrylic acid copolymers, wherein the aqueous solution has a pH of about 8.0 to 13.0.

2. A solid pharmaceutical preparation, which contains a composition comprising an aqueous solution of a heat-labile active vitamin D$_2$ compound being dispersed in a basic polymer selected from the group consisting of vinyl acetate polymers and (meth) acrylic acid copolymers, wherein the aqueous solution has a pH of about 8.0 to 13.0.

3. The solid pharmaceutical preparation according to claim 2, wherein the solid pharmaceutical preparation is in the form of tablets, capsules, granules or powder.

4. A composition of a heat-labile active vitamin D$_2$ compound, which comprises an excipient which is soluble in an organic solvent, a heat-labile active vitamin D$_2$ compound and a basic substance selected from the group consisting of alkali metal salts of a C$_2$-C$_6$ organic carboxylic acid, alkaline earth metal oxides, alkali metal carbonates or hydrogencarbonates, alkaline earth metal carbonates, alkali metal phosphates and alkali metal pyrophosphates.

5. The composition according to claim 4, wherein the heat-labile active vitamin D$_2$ compound and the basic substance are dispersed in an excipient which is soluble in an organic solvent.

6. A solid pharmaceutical preparation, which contains a composition comprising an excipient which is soluble in an organic solvent, a heat-labile active vitamin D$_2$ compound and a basic substance selected from the group consisting of alkali metal salts of a C$_2$-C$_6$ organic carboxylic acid, alkaline earth metal oxides, alkali metal carbonates or hydrogencarbonates, alkaline earth metal carbonates, alkali metal phosphates and alkali metal pyrophosphates.

7. The solid pharmaceutical preparation according to claim 6, wherein the solid pharmaceutical preparation is in the form of tablets, capsules, granules or powder.

8. A composition of a heat-labile active vitamin D$_2$ compound, which comprises a finely pulverized heat-labile active vitamin D$_2$ compound being dispersed homogeneously in a basic substance selected from the group consisting of alkali metal salts of a C$_2$-C$_6$ organic carboxylic acid, alkaline earth metal oxides, alkali metal carbonates or hydrogencarbonates, alkaline earth metal carbonates, alkali metal phosphates and alkali metal pyrophosphates and an excipient which is soluble in water.

9. A solid pharmaceutical preparation, which contains a composition comprising a finely pulverized heat-labile active vitamin D$_2$ compound being dispersed homogeneously in a basic substance selected from the group consisting of alkali metal salts of a C$_2$-C$_6$ organic carboxylic acid, alkaline earth metal oxides, alkali metal carbonates or hydrogencarbonates, alkaline earth metal carbonates, alkali metal phosphates and alkali metal pyrophosphates and an excipient which is soluble in water.

10. The solid pharmaceutical preparation according to claim 9, wherein the solid pharmaceutical preparation is in the form of tablets, capsules, granules or powder.

11. A method of producing a composition which comprises incorporating a finely pulverized heat-labile active vitamin D$_2$ compound into a basic substance selected from the group consisting of alkali metal salts of a C$_2$-C$_6$ organic carboxylic acid, alkaline earth metal oxides, alkali metal carbonates or hydrogencarbonates, alkaline earth metal carbonates, alkali metal phosphates and alkali metal pyrophosphates and an excipient which is soluble in water.

12. The method according to claim 11, wherein incorporating is performed in a solvent which does not dissolve the heat-liable active vitamin D$_2$ compound and dissolves the excipient which is soluble in water.

13. The method according to claim 12, wherein the solvent is water.

14. A composition of a heat-labile active vitamin $D_2$ compound, which comprises a heat labile active vitamin $D_2$ compound being dispersed in a vinyl acetate polymer.

15. The composition of claim 14, wherein the vinyl acetate polymer is polyvinylacetal diethylaminoacetate.

16. A solid pharmaceutical preparation, which contains a composition comprising a heat-labile active vitamin $D_2$ compound being dispersed in a vinyl acetate polymer.

17. The solid pharmaceutical preparation of claim 16 wherein the polymer is polyvinylacetal diethylaminoacetate.

* * * * *